United States Patent
Sagalovich et al.

[11] Patent Number: 5,913,832
[45] Date of Patent: Jun. 22, 1999

[54] URINE COLLECTION SYSTEM

[75] Inventors: Emil Sagalovich, Thornhill; Alexei Bogdan, Bolton, both of Canada

[73] Assignee: Inventamed International Inc., Oakville, Canada

[21] Appl. No.: 08/523,860

[22] Filed: Sep. 6, 1995

[51] Int. Cl.⁶ ........................................ A61B 5/00
[52] U.S. Cl. ............................. 600/573; 600/77; 600/1; 604/317
[58] Field of Search ................. 1287/760, 767, 1287/762, 771; 604/317, 318, 319

[56] References Cited

U.S. PATENT DOCUMENTS

| | | | |
|---|---|---|---|
| 3,625,654 | 12/1971 | Van Duyne | 128/760 |
| 4,393,881 | 7/1983 | Shah | 128/760 |
| 4,773,419 | 9/1988 | Tountas | 606/202 |
| 4,819,280 | 4/1989 | Rickard | 4/301 |
| 4,824,071 | 4/1989 | Duffy et al. | 249/117 |
| 4,960,130 | 10/1990 | Guirguis | 128/760 |
| 5,117,515 | 6/1992 | White, Jr. et al. | 4/661 |
| 5,210,884 | 5/1993 | Redford | 4/348 |
| 5,339,829 | 8/1994 | Thieme et al. | 128/760 |
| 5,352,410 | 10/1994 | Hansen et al. | 422/58 |
| 5,393,496 | 2/1995 | Seymour . | |
| 5,496,290 | 3/1996 | Ackerman | 604/268 |

FOREIGN PATENT DOCUMENTS

| | | | |
|---|---|---|---|
| 5111476 | 5/1993 | Japan | 600/573 |

*Primary Examiner*—Cary O'Connor
*Assistant Examiner*—Pamela L. Wingood
*Attorney, Agent, or Firm*—Chadbourne & Parke LLP

[57] ABSTRACT

A urine collection system has a disposable pan that attaches to a toilet bowl or seat. The pan has overflow holes to dispose of excess urine. A flexible tube extends from the pan to a collection unit having a spring-loaded syringe that semi-automatically withdraws a urine sample from the pan. The collected urine is then transported in the syringe for further processing.

16 Claims, 5 Drawing Sheets

URINE COLLECTION SYSTEM

BACKGROUND OF THE INVENTION

The present invention relates generally to a urine collection system and, more particularly to a urine collection pan attachable to a toilet and connected by a tube to a semi-automatic collection unit having a spring-operated syringe.

Present medical services worldwide do not provide any convenient means for millions of women who need to submit urine samples for analysis. Women in many countries must use a container that is identical to that used by men for the same purpose. The urine is typically collected by passing a cup through the urine stream. The urine is then transferred from the cup to a container for transport prior to processing.

U.S. Pat. No. 5,352,410 to Hansen et al. discloses a device for collecting and testing fluid specimens, including urine. Several embodiments of invention the include a barrel and plunger arrangement which inserts an absorbent material into a fluid stream or into a container such as a cup which holds the fluid to be collected. Once the fluid sample is absorbed, the absorbent material is withdrawn into the barrel and the barrel is sealed.

U.S. Pat. No. 5,339,829 to Thieme et al. discloses a syringe-type device for collecting oral fluids. The device includes an absorbent pad impregnated with a hypertonic solution which increases the recovery of a test substance such as immunoglobulin. To recover the oral fluid, the absorbent pad is placed within the oral cavity for approximately 40 seconds to two minutes.

U.S. Pat. No. 4,960,130 to Guirguis discloses a device for collecting, processing and analyzing biological fluids such as urine. The device includes a transporter assembly connected to a resin/sample container. The combined assembly and container are inserted into a cylindrical tube containing a urine specimen. Movement of the assembly and the container down the cylindrical tube functions to separate and collect the fluid and particulate components in the urine specimen.

U.S. Pat. No. 4,824,071 to Duffy et al. discloses a device for making a customized female urine receptacle for incontinent females. The customized receptacle having a rim with a surface contour matching the uro-genital tissue which it contacts. The receptacle is then connected to a collection means such as a bag which is strapped to the user's leg.

U.S. Pat. No. 4,819,280 to Rickard discloses a portable urinal and flush system. The portable urinal can be a bottle having male and female adapters or the bottle itself can be made in both male and female configurations.

U.S. Pat. No. 5,393,496 to Seymour discloses a saliva sampling device. This device includes a saliva collector which is a piece of filter paper that is inserted in the user's mouth to collect the saliva.

The present invention is directed to the problem of improving the collection of urine from a urine stream and the semi-automatic transfer of that urine to a container for processing.

SUMMARY OF THE INVENTION

The present invention solves this problem by providing a urine collection system having a disposable pan that attaches to the toilet bowl or seat. The pan has openings through which excess urine can overflow into the toilet bowl. The open end of a flexible tube rests at or near the bottom of the pan. The tube is held in position near the edge of the pan and the other end of the tube is connected to the inlet end of a spring-loaded syringe which functions as a collection unit. After the urine is deposited in the pan, a clip on the syringe is released and the action of the spring causes the plunger of the syringe to retract, filling the syringe tube with urine. Thereafter, the syringe is easily detached from the tube so that the syringe containing the urine sample can be transported for processing.

The spring-loaded action of the syringe enables the collection of the urine sample to be semiautomatic. The collection unit is transportable, sterile, non-leaking, and easy to use. A lab technician does not have to use any additional devices or instruments to process the urine sample for different tests since the lab technician will use the collection unit for the processing of the urine samples. Although the urine collection system improves the urine collection process for women, it can be easily used by both men and women. It can also be used without a toilet when the shape of the pan is modified and the overflow holes are removed. This modification in the pan permits its use in beds or in situations where there is no convenient access to toilets.

DETAILED DESCRIPTION

Figure 1:
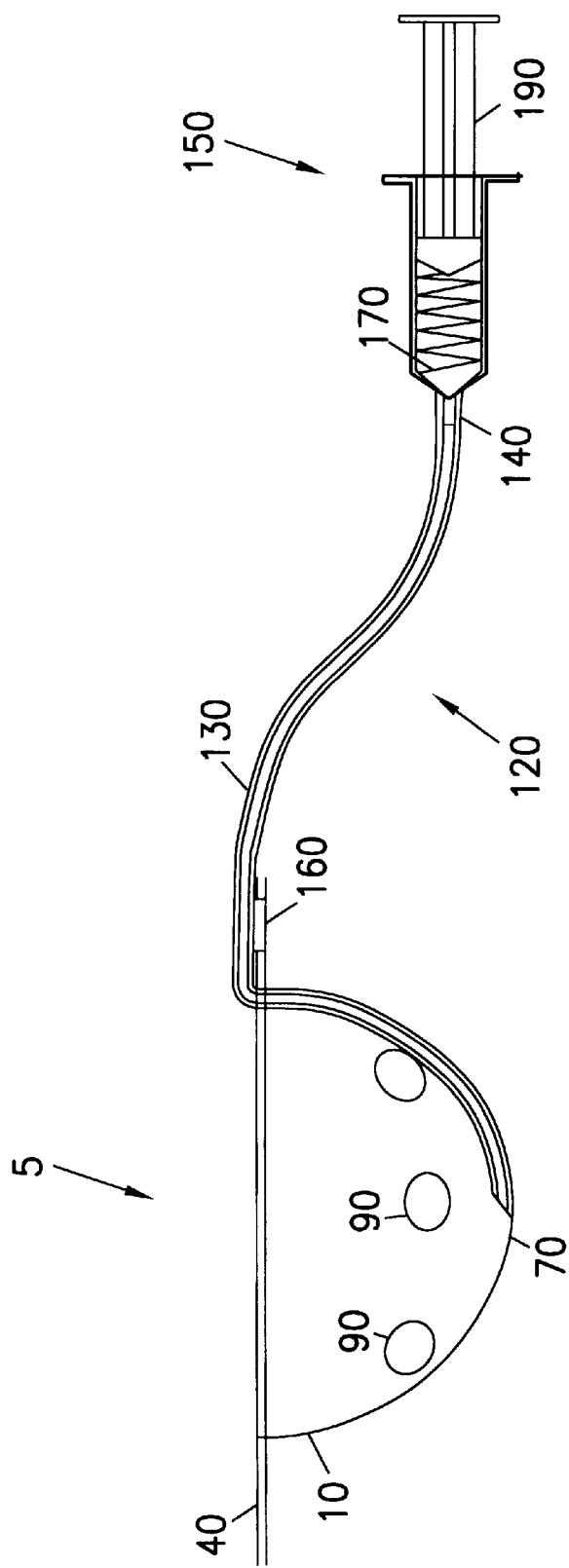
FIG. 1 is a cross-sectional side view of an embodiment of the urine collection system constructed according to the principles of the present invention.
Figure 2:
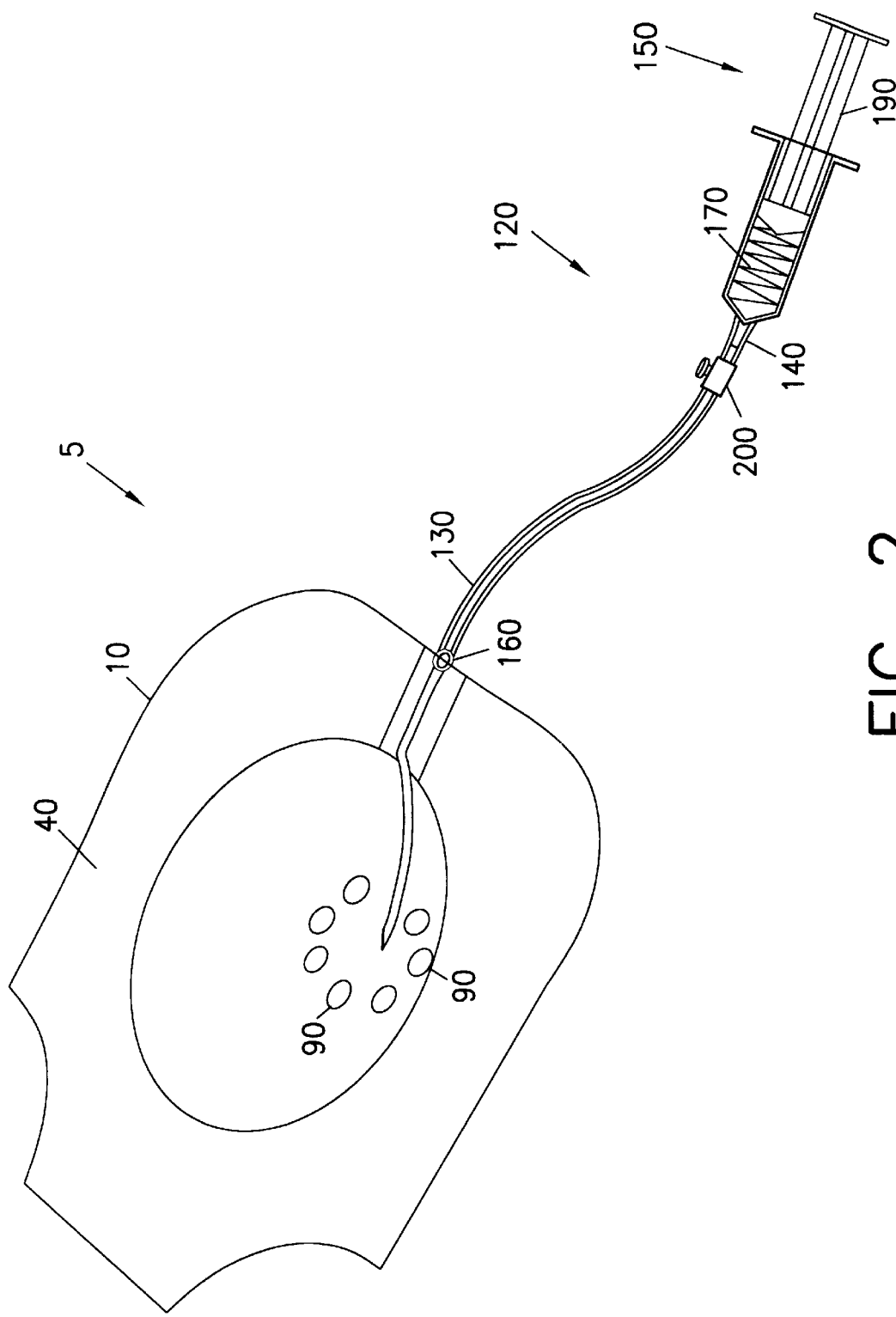
FIG. 2 is a top view of the embodiment of FIG. 1.

As illustrated in FIGS. 1 and 2, in the preferred embodiment of the present invention, the urine collection system 5 consists of a disposable or water-dissolving pan 10 for one-time use. A water dissolving gel may be used for the pan. The gel must be stable during the collection of urine and must not react with the urine to contaminate the urine sample. This part easily fits on all types of toilets 20 and it is configured to allow accumulation of a urine sample from a urine stream. The pan 10 is generally a concave, hemispherical pan having a rim 40 that permits the pan to be supported by a toilet bowl rim or a toilet seat so that the bottom surface 70 of the pan does not contact the water in the toilet. The lower portion of the pan surface has holes 90 located so that excess urine overflows into the toilet bowl. The pan 10 may be disposable, dissolvable in water with time or reusable. The pan 10 may also be constructed without the overflow holes 90.

In an alternate embodiment, the pan 10 is not supported by the toilet bowl seat or rim and the pan has a flattened bottom configuration that contacts the water surface in the toilet bowl. The pan 10 is also shaped to fit and rest against the inside of the toilet bowl and has no overflow holes. When used inside a toilet bowl, the pan may also have air captured cavities to permit the pan to float on the surface of the toilet water. The flattened configuration also permits use of the pan without placement in a toilet bowl. Such applications may include use of the pan in bed or in other locations without convenient access to toilets. For applications within the toilet bowl, a floatation means may be desirable to support the pan in a floating position on the surface of the toilet water. This flotation means may be a number of mechanisms. For example, the rim of the pan may be designed to include enclosed air cavities for buoyancy. In addition, inflatable devices may be attached to the pan, or the pan could be made of floatable material. In addition, any number of conventionally recognized flotation means may be employed.

Figure 3:
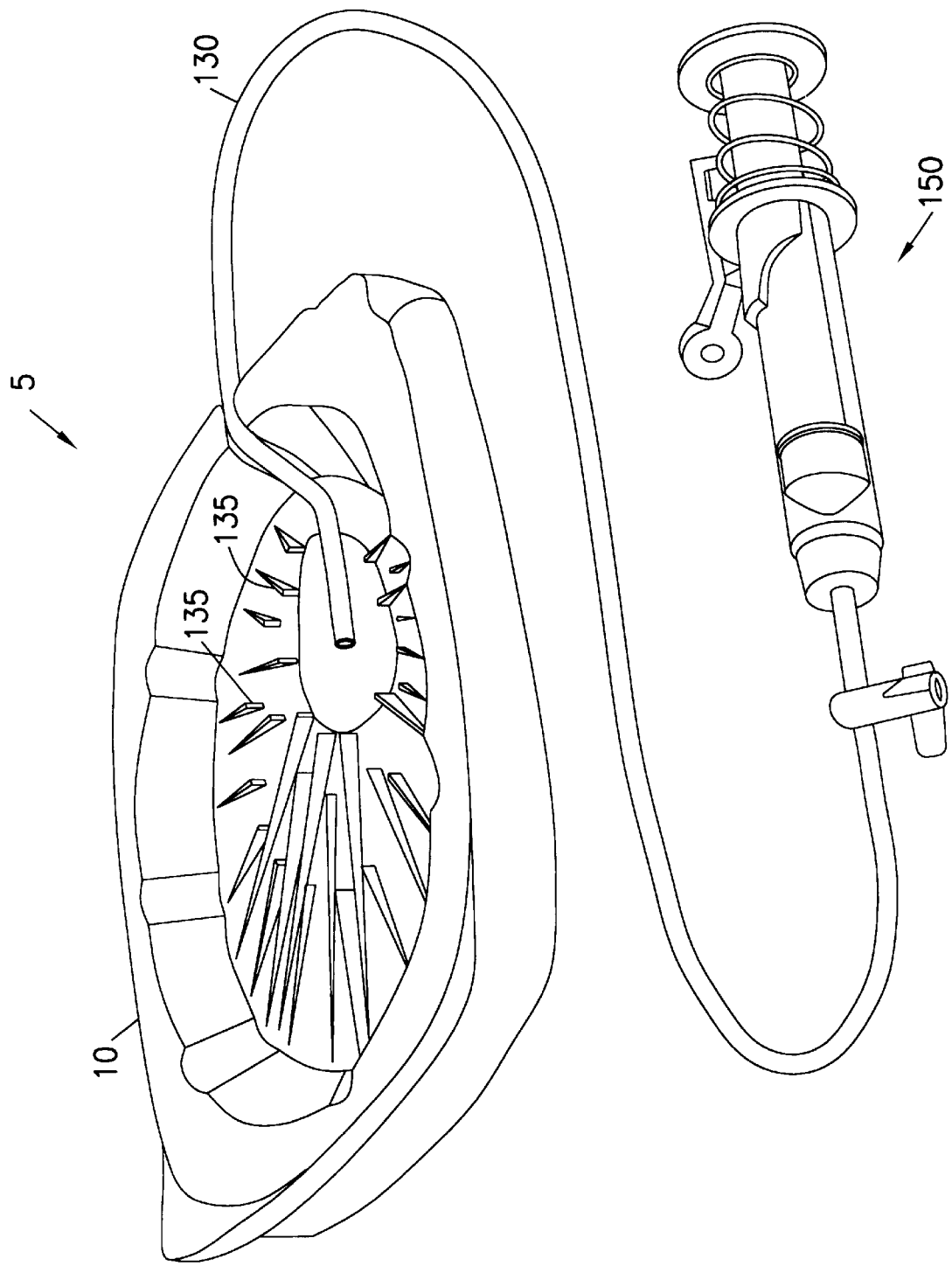
FIG. 3 is a perspective view of a raised ridge texture on the inner surface of the pan.

A collection portion 120 of the preferred embodiment of the urine collection system has a flexible tube 130 with one end positioned at the bottom of the pan 10 and the other end attached to the inlet portion 140 of a syringe 150. The tube 130 may be fixedly or removably attached 160 to the pan to hold it in position. The attachment 160 may be any suitable means such as with glue, snaps, clips or any other means which does not interfere with flow of the urine through the tube 130. Referring to FIG. 3, a portion of the inner surface of the pan 10 may have a raised ridge texture 135 which is generally radially aligned to aid in directing the urine toward the end of the tube 130 positioned in the bottom of the pan 10. The raised ridge texture 135 may also act to reduce the amount of splash associated with the urine stream. Although a raised ridge texture is illustrated, a texture may also be grooved or formed into the surface of the pan to aid in directing the urine to the end of the tube.

Figure 4:
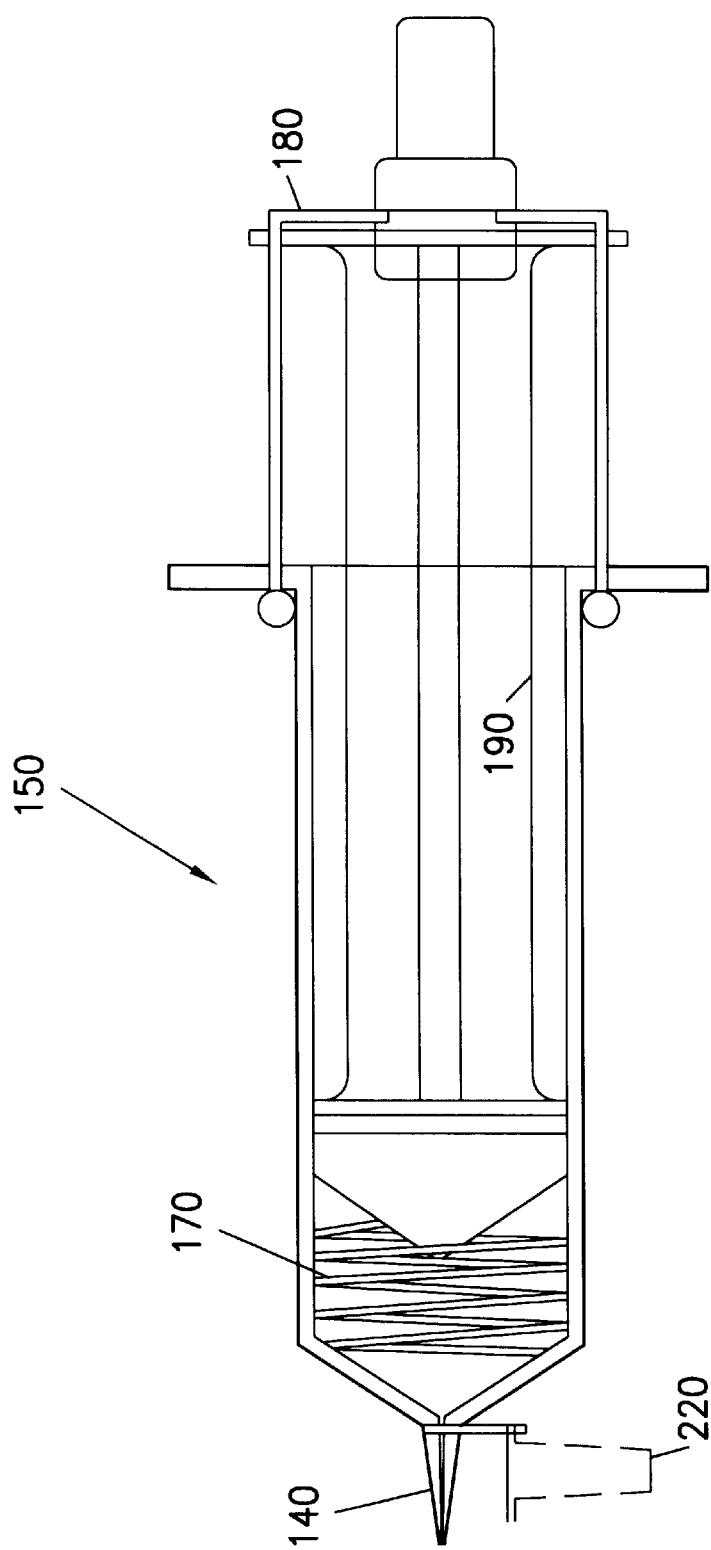
FIG. 4 is a cross-sectional side view of an embodiment of a spring-loaded syringe with the spring in a compressed state.
Figure 5:
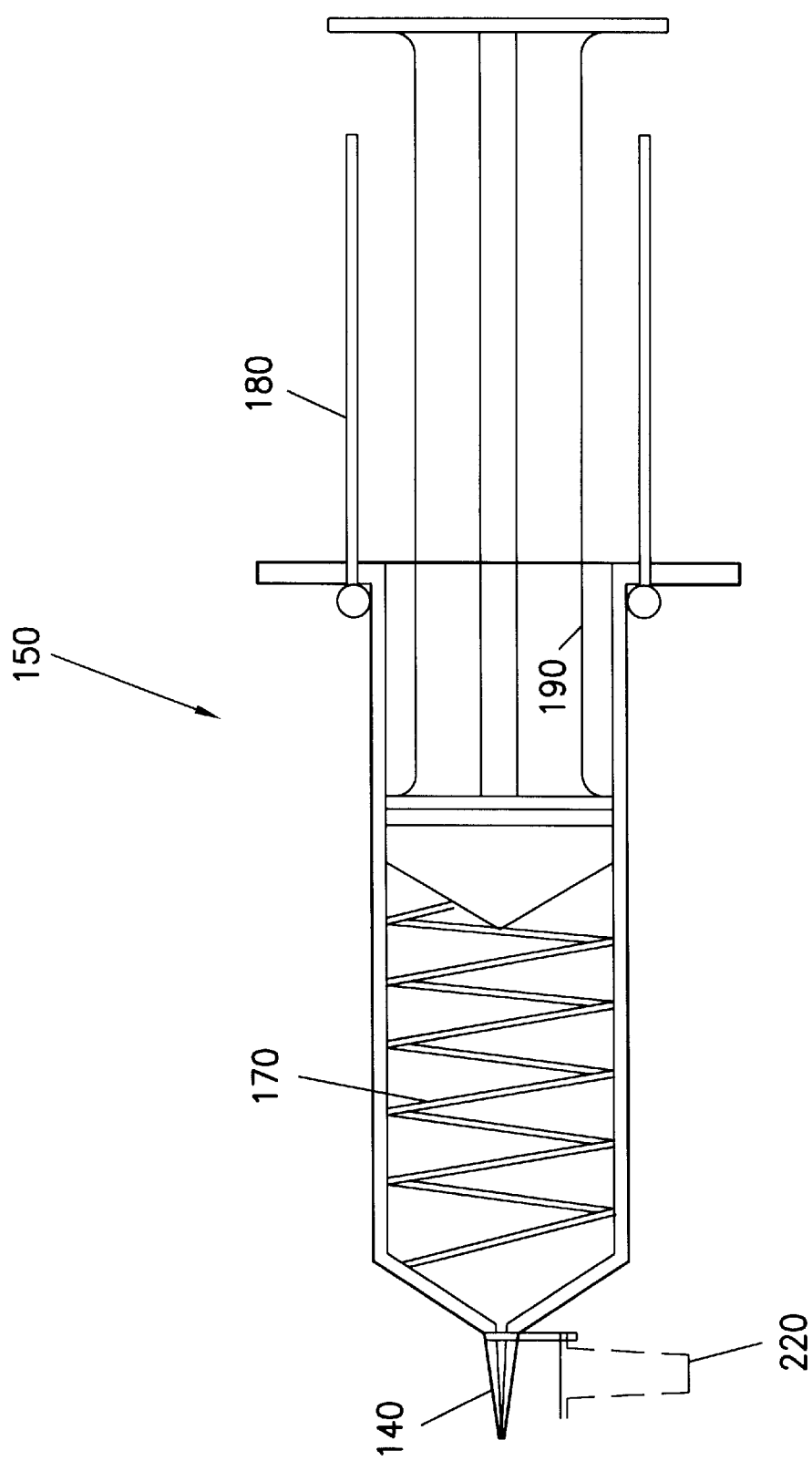
FIG. 5 is a cross-sectional view of the syringe of FIG. 4 with the spring in an expanded state.

Referring to FIG. 4, the syringe 150 is spring-loaded, with the spring 170 held in compression within the syringe 150 by a clip 180 which holds the syringe plunger 190 down. Although a clip is used in the preferred embodiment, it is understood by those skilled in the art that any suitable restraining means, such as a cap or a strip of adhesive material, may be used to hold the plunger down. In addition, although the preferred embodiment illustrates a spring 170 which is internally disposed in the syringe 150, the spring may also be located on the outside of the syringe 150 and attached to the plunger 190. Referring to FIG. 5, when the urine sample is ready for collection, the clip 180 is released allowing the spring 170 to expand and push the plunger 190 out to affect suction of the urine into the syringe 150. The urine collected in the syringe 150 is then transported to a laboratory for processing. If desired, flow of the urine to and from the syringe 150 can be controlled by a valve 200 at the inlet portion 140 of the syringe.

After urination, a woman activates the collection part 120 of the urine collection system which is attached to the disposable pan 10 of the device. At this point, the process of collecting urine becomes automatic and it takes place without participation of the woman. The collection part 120 then is simply detached from the rest of the system. After detachment of the collection part, the remaining pan 10 can be disposed into a stand-alone container. When the tube 130 is removed from the inlet portion 140 of the syringe, the inlet portion 140 may be covered with a cap 220.

Though the present invention has been described with reference to specific embodiments selected for the purpose of illustration, it should be understood that numerous modifications could be applied by those skilled in the art without departing from the basic concept and scope of the present invention.

What is claimed is:

1. A urine collection system for collecting urine from a urine stream, comprising:
   a pan detachably attachable to a toilet seat for receiving urine from the urine stream, wherein the pan has a bottom and generally vertical sides;
   a flexible tube having a first end and a second end, wherein the first end of the tube is disposed in the bottom of the pan and the flexible tube is attached to the pan to hold the flexible tube in the desired position; and
   a syringe, wherein the syringe further includes:
      a container having an inlet portion, wherein the second end of the flexible tube is detachably connected to the inlet portion of the container;
      a plunger slidably disposed within the container,
      a spring connected to the plunger so that the spring is compressed as the plunger slides into the container; and
      a detachable restraining means for holding the plunger against the spring to maintain the spring in compression until the restraining means is detached.

2. The urine collection system of claim 1, wherein a portion of the upper surface of the bottom of the pan has a texture for directing urine to the first end of the flexible tube.

3. The urine collection device of claim 2, wherein the texture includes a plurality of generally radially aligned ridges.

4. The urine collection system of claim 1, wherein the pan is a water-dissolving gel that is stable during urine collection and non-reactive with the urine so that contamination of the urine is prevented.

5. The urine collection system of claim 1, further comprising a valve at the inlet portion of the container to control the flow of urine through the inlet portion.

6. The urine collection system of claim 5, further comprising a cap that is removably attached to the inlet portion of the container when the second end of the flexible tube is detached from the inlet portion.

7. The urine collection system of claim 1, wherein the bottom of the pan is generally flat.

8. The urine collection system of claim 7, wherein a portion of the upper surface of the bottom of the pan has a texture for directing urine to the first end of the flexible tube.

9. The urine collection device of claim 2, wherein the texture includes a plurality of generally radially aligned ridges.

10. The urine collection system of claim 7, further comprising a valve at the inlet portion of the container to control the flow of urine through the inlet portion.

11. The urine collection system of claim 10, further comprising a cap that is removably attached to the inlet portion of the container when the second end of the flexible tube is detached from the inlet portion.

12. The urine collection system of claim 7, wherein the sides of the pan are generally shaped to conform to the interior dimensions of a toilet bowl so that the toilet bowl supports the pan when the pan is positioned in a toilet.

13. The urine collection system of claim 12, further comprising a valve at the inlet portion of the container to control the flow of urine through the inlet portion.

14. The urine collection system of claim 13, further comprising a cap that is removably attached to the inlet portion of the container when the second end of the flexible tube is detached from the inlet portion.

15. The urine collection system of claim 7, wherein the pan further includes a float means.

16. The urine collection system of claim 14, wherein the pan is a water-dissolving gel that is stable during urine collection and non-reactive with the urine so that contamination of the urine is prevented.

* * * * *